United States Patent [19]
Kaneko et al.

[11] Patent Number: 5,292,891
[45] Date of Patent: Mar. 8, 1994

[54] OPTICALLY ACTIVE 2,2-DIMETHYL-1,3-DIOXIN-4-ONES AND METHOD FOR PREPARING SAME AND METHOD FOR PREPARING OPTICALLY ACTIVE COMPOUND FOR SYNTHESIS OF PHYSIOLOGICALLY ACTIVE SUBSTANCE AND OPTICALLY ACTIVE INTERMEDIATE COMPOUND

[75] Inventors: Chikara Kaneko; Masayuki Sato, both of Sendai, Japan

[73] Assignee: Chisso Corporation, Osaka, Japan

[21] Appl. No.: 991,551

[22] Filed: Dec. 15, 1992

Related U.S. Application Data

[63] Continuation-in-part of Ser. No. 836,425, Feb. 18, 1992, Pat. No. 5,256,800, and a continuation-in-part of Ser. No. 836,426, Feb. 18, 1992, abandoned.

[30] Foreign Application Priority Data

Feb. 21, 1991 [JP] Japan .................................. 3-047285
Feb. 21, 1991 [JP] Japan .................................. 3-047286

[51] Int. Cl.$^5$ ................. C07D 301/27; C07D 309/10; C07D 309/30
[52] U.S. Cl. .................................... 549/273; 549/292; 549/294; 549/518; 549/561
[58] Field of Search ............... 549/273, 274, 292, 294, 549/518, 561

[56] References Cited

PUBLICATIONS

Sakaki et al., Chemistry Letters, No. 6, Jun. 1990, pp. 901–904.
Chisso Corp., Patent Abstracts of Japan, vol. 14, No. 439 (C-761) 19 Sep. 1990 JP-A-2 171 192 2 Jul. 1990.
Sakaki et al., Tetrahedron, vol. 47, No. 32, pp. 6197–6214 (1991).
Sato et al., Chemical Abstracts, vol. 116 (1992) Abstract No. 41376j.
Sakaki et al., J. Chem. Soc., Chem. Commun. (1991) pp. 434–435.
Sakaki et al., Tetrahedron: Asymmetry, vol. 2, No. 5 pp. 343–346 (1991).

*Primary Examiner*—Marianne M. Cintins
*Assistant Examiner*—Michael B. Hydorn
*Attorney, Agent, or Firm*—Wenderoth, Lind & Ponack

[57] ABSTRACT

There are provided novel and optically active 2,2-dimethyl-1,3-dioxin-4-ones which are useful as starting materials for physiologically active compounds, functional materials or the like. Provided are optically active 5,6-epoxyhexanoic acid esters and novel optically active 6-substituted tetrahydropyran-2-one derivatives. That is, optically active 6-chloromethyltetrahydropyran-2-one can be synthesized by lactonizing optically active 2,2-dimethyl-6-(3-chloro-2-hydroxypropyl)-1,3-dioxin-4-one to form optically active 6-chloromethyltetrahydropyran-2,4-dione; reacting the thus formed compound with hydrogen in the presence of a catalyst to obtain optically active 6-chloromethyl-4-hydroxytetrahydropyran-2-one; subjecting this compound to a dehydration reaction, thereby obtaining optically active 6-chloromethyldihydropyran-2-one; reacting this compound with hydrogen in the presence of a catalyst to form optically active 6-chloromethyltetrahydropyran-2-one; and then treating this compound under basic conditions to prepare an optically active 5,6-epoxyhexanoic acid ester represented by the formula (6)

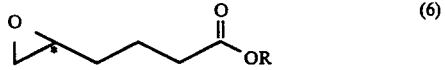

(wherein the symbol * represents an asymmetric carbon atom, and R is a methyl group or an ethyl group).

6 Claims, No Drawings

OPTICALLY ACTIVE 2,2-DIMETHYL-1,3-DIOXIN-4-ONES AND METHOD FOR PREPARING SAME AND METHOD FOR PREPARING OPTICALLY ACTIVE COMPOUND FOR SYNTHESIS OF PHYSIOLOGICALLY ACTIVE SUBSTANCE AND OPTICALLY ACTIVE INTERMEDIATE COMPOUND

This application is a continuation-in-part of application Ser. No. 07/836,425, filed Feb. 18, 1992, now U.S. Pat. No. 5,256,800 a continuation-in-part Ser. No. 07/836,426, filed Feb. 18, 1992 now abandoned.

The present application is divided into two parts. Part I provides a disclosure of optically active 2,2-dimethyl-1,3- dioxin-4-ones and method for preparing them. Part II provides a disclosure of the method for preparing optically active compound for synthesis of physiologically active substance and optically active intermediate compound.

BACKGROUND OF THE INVENTION (i) Field of the Invention

The present invention relates to optically active 1,3-dioxin-4-Ones which are useful as starting materials of physiologically active compounds, functional materials and the like, and a method for preparing the same.

(ii) Description of the Prior Art

As compounds of 1,3-dioxin-4-ones, racemic compounds represented by the formula

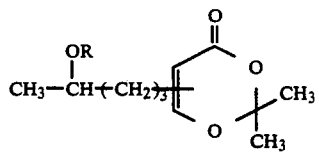

are described in B. Damin., J. Org. Chem., 46 (17), 3552 (1981) and N. A. Petasis., J. Chem. Soc., Chem, Commun., 11, 836 (1990), but optically active compounds analogous to these compounds have not been known.

On the other hand, in order to obtain physiologically active compounds, functional materials and the like, optically active compounds are necessary as starting materials. For example, in the case that the physiologically active compound, the functional material or the like has asymmetric carbon atom, plural isomers are present, but usually one of these isomers has advantageous characteristics Therefore, when a racemic modification or a compound having a low optical purity is used as the starting material, the resultant product cannot exert sufficiently physiological activity or functional properties. Thus, it is desired that the compound which will be fed as the starting material also has the sufficiently optical purity.

SUMMARY OF THE INVENTION

In view of the above-mentioned problems, an object of the present invention is to provide novel and optically active 1,3-dioxin-4-ones which are useful as starting materials of physiologically active compounds, functional materials or the like.

Another object of the present invention is to provide a method for preparing these novel and useful compounds.

The present inventors have repeatedly and intensively researched to achieve the above-mentioned objects, and as a result, they have succeeded in obtaining novel and optically active 1,3-dioxin-4-ones, and the present invention has been completed.

An optically active 1,3-dioxin-4-one which is the first aspect of the present invention is characterized by having the formula (1):

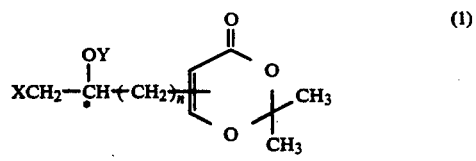

A method for preparing an optically active compound which is the second aspect of the present invention is characterized by reacting a racemic 1,3-dioxin-4-one represented by the formula (2)

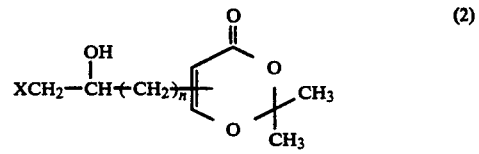

with vinyl acetate in the presence of lipase to resolve the racemic compound into an optically active compound represented by the formula (3)

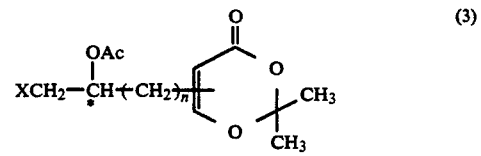

and an optically active compound represented by the formula (4)

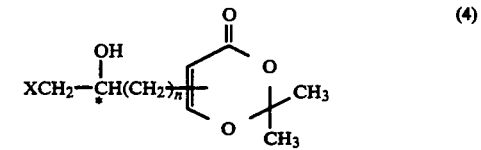

which is an antipode of the compound represented by the formula (3)

A method for preparing an optically active compound which is the third aspect of the present invention is characterized by hydrolyzing a racemic 1,3-dioxin-4-one represented by the formula (5)

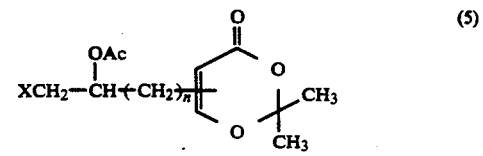

in the presence of lipase to resolve the racemic compound into an optically active compound represented by the formula (3) and an optically active compound represented by the formula (4) which is an antipode of the compound represented by the formula (3).

A method for preparing an optically active 1,3-dioxin-4-one which is the fourth aspect of the present invention is characterized by bringing a compound represented by the formula (6)

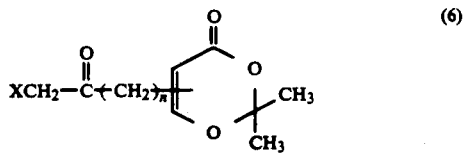

into contact with baker's yeast to sterically and selectively reduce this compound and to thereby form an optically active 1,3-dioxin-4-one.

In the formulae (1) to (6), n is a value of 1 to 3, X is a hydrogen atom, a benzyloxy group, a chlorine atom or $N_3$, and Y is a hydrogen atom or an acetyl group. The substituent in each formula is present at the 5-position or 6-position. When n is 1, X is the benzyloxy group, the chlorine atom or $N_3$, and the substituent is present at the 6-position. When n is 2, X is the hydrogen atom, and the substituent is present at the 5-position. And when n is 3, X is the hydrogen atom, and the substituent is present at the 6-position. The symbol * represents an asymmetric carbon atom.

DETAILED DESCRIPTION OF THE INVENTION

Compounds represented by the formulae (2), (5) and (6) which are starting materials for use in a manufacturing method of the present invention can be suitably prepared in accordance with the following route, for example, in the case of n=1:

(9) in the presence of a base typified by lithiumdiisopropylamide (LDA) to derive an acyl compound [having the formula (6) in which n is 1, and X is a benzyloxy group or a chlorine atom], and the acyl compound is then reacted with sodium azide ($NaN_3$) in dimethylformamide (DMF) to obtain an azide [having the formula (6) in which n is 1 and X is $N_3$]. This product can be used as a material for an asymmetrical reduction using baker's yeast. Next, the compound of the formula (6) is reacted with a reducing agent such as sodium borohydride or lithium aluminum hydride to carry out a reduction reaction, whereby a racemic compound represented by the formula (2') is derived.

Furthermore, the compound represented by the formula (2') is reacted with an acetylating agent such as acetyl chloride or acetic anhydride in the presence of a basic catalyst such as pyridine, triethylamine or dimethylaminopyridine to carry out acetylation, so that a racemic compound represented by the formula (5') is formed. These compounds represented by the formulae (2') and (5') can be used as starting materials for the preparation of the optically active compounds of the second and third aspects of the present invention.

For example, in the case of compounds having the formulae (2), (5) and (6) in which n is 3, the reaction is as follows:

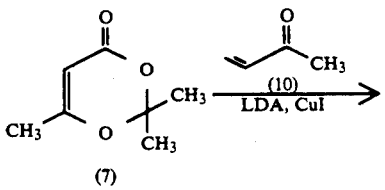

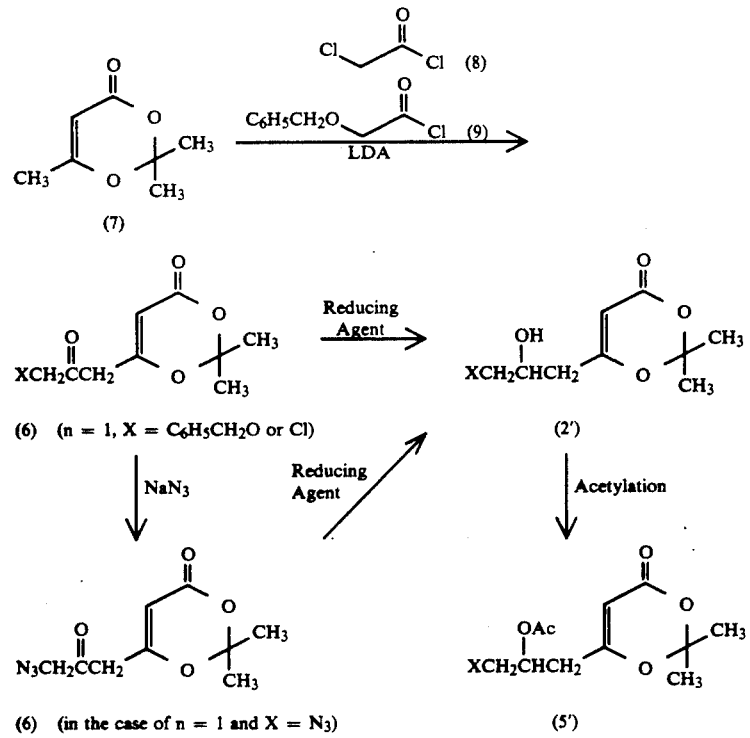

That is, 6-methyl-1,3-dioxin-4-one (7) is reacted with chloroacetyl chloride (8) or benzyloxyacetyl chloride -continued

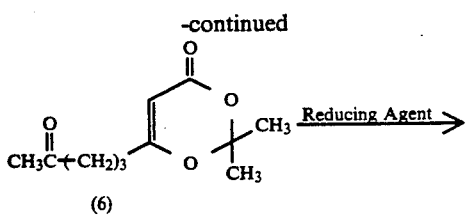

(6)

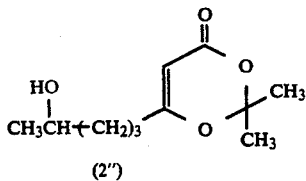

(2")

That is, 6-methyl-1,3-dioxin-4-one (7) is reacted with α,β-unsaturated ketone (10) in the presence of a base such as LDA and copper iodide to form a compound having a formula (6) in which n is 3. This compound can be further be subjected to a reduction reaction using a reducing agent such as sodium borohydride or lithium aluminum hydride, thereby deriving a racemic compound represented by the formula (2").

Reference will be made to a method for preparing the optically active compound of the second aspect of the present invention.

The compound of the formula (2) is reacted with vinyl acetate (11) in the presence of lipase to selectively acylate either antipode alone to thereby resolve the compound into an optically active ester compound of the formula (3) and an optically active alcoholic compound which is represented by the formula (4) and which is an antipode of the compound having the formula (3), as follows:

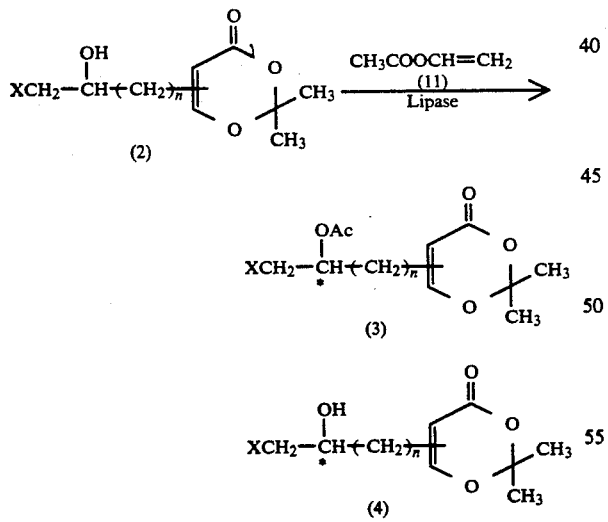

In the above-mentioned preparation process, any kind of lipase can be used, so long as it has the ability by which either antipode is selectively and exclusively acylated, and above all, Lipase MY (made by The Meito Sangyo Co., Ltd.; origin *Candida cylindracea*) and Lipase PS (made by Amano Pharmaceutical Co., Ltd., origin *Pseudomonas fluorescens*) are preferable. A preferable reaction solvent is benzene, but the reaction can be carried out without using any solvent. A reaction temperature may be room temperature, and a reaction time is from 4 to 9 hours.

After the reaction has been carried out in this way, lipase can be removed by a usual filtration, but it can be reutilized as it is. The reaction product obtained in the form of the filtrate can be separated into an optically active alcoholic compound represented by the formula (4) and an optically active ester compound which is represented by the formula (3) and which is the antipode of the compound having the formula (4) by operation such as vacuum distillation or column chromatography. Furthermore, the optically active ester compound of the formula (3) obtained above is deacetylated by hydrolysis using lipase to obtain an optically active alcohol which is the antipode of the above-mentioned optically active alcoholic compound.

Reference will be made to a method for preparing the optically active compound of the third aspect of the present invention.

A racemic compound represented by the formula (5) can be used as a starting material and subjected to a stereo selective hydrolysis reaction to resolve the racemic compound into optically active compounds represented by the formula (3) and (4), as follows:

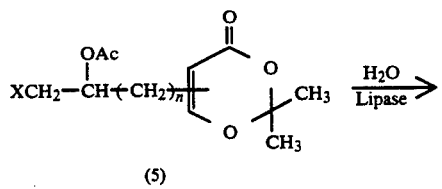

(5)

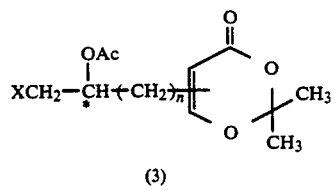

(3)

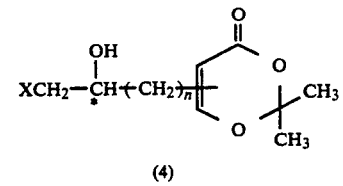

(4)

Either antipode of the compound of the formula (5) can be selectively and exclusively hydrolyzed by the action of lipase in a phosphoric acid buffer solution to resolve the compound into the optically active compounds represented by the formulae (3) and (4). Any kind of lipase can be here used, so long as it has the ability by which either antipode is selectively and exclusively hydrolyzed, and above all, Lipase MY (made by The Meito Sangyo Co.; Ltd.; origin *Candida cylindracea*) and Lipase PS (made by Amano Pharmaceutical Co., Ltd., origin *Pseudomonas fluorescens*) are preferable. The phosphoric acid buffer solution which can be used preferably has a pH of about 7.2, and it can be mixed with about 30% of acetone.

After this reaction, the resultant reaction product can be taken out by a usual extraction and then subjected to vacuum distillation or column chromatography to resolve it into the optically active alcoholic compound represented by the formula (4) and the optically active ester compound of the formula (3), and the obtained optically active ester compound of the formula (3) can be deacetylated by hydrolysis using lipase to obtain an optically active alcohol which is the antipode of the above-mentioned optically active alcoholic compound.

Reference will be made to a method for preparing an optically active 1,3-dioxin-4-one of the fourth aspect of the present invention.

A compound represented by the formula (6) is subjected to a stereo selective reduction reaction using baker's yeast as an asymmetrical reducing agent to derive a 1,3-dioxin-4-one represented by the formula (1) in which Y is H, as follows:

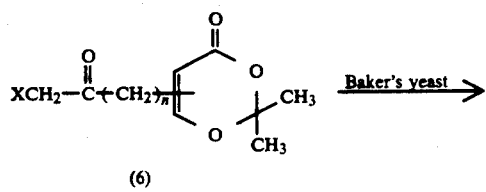

(6)

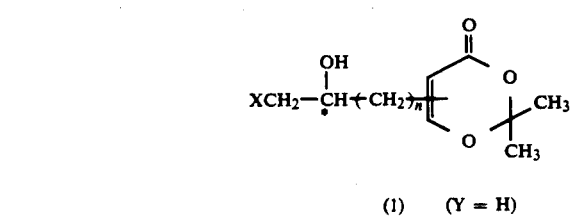

(1)   (Y = H)

As the asymmetrical reducing agent which can be used in the present invention, the baker's yeast (*Saccharomyces cerevisiae*) is preferable, but any kind of reducing agent can be employed, so long as it can act on a substrate and achieve the asymmetrical reduction reaction (e.g., *Kloechera saturnus*, *Lipomyces starkeyi*, *Saccharomyces delbrueckii*, *Saccharomyces fermentati*, *Candida humicola*, *Candida cuillermondi* and *Candida albicans*).

The asymmetrical reduction using the baker's yeast can be achieved by effectively bringing the baker's yeast into contact with the substrate and a carbon source usually in water, and this reaction can be carried out in an open system without using any special reaction devices. Furthermore, water which can be used in the reaction may be tap water, and any particular treatment is not required for water. Preferable examples of the carbon source include carbohydrates such as saccharose and glucose, and an organic acid such as acetic acid and an alcohol can also be used on occasion.

In the present invention, the reaction temperature is suitably from 15° to 45° C., and the particularly preferable reaction temperature is from 25° to 35° C., depending upon the kind of substrate to be used. The reaction time is suitably from 1 to 100 hours, similarly depending upon the kind of substrate. The concentration of the substrate is suitably from 0.01 to 20% by weight, preferably from 0.5 to 5% by weight.

The removal of the desired product from the reaction product obtained through the asymmetrical reduction can be effectively achieved by extraction with an organic solvent such as dichloromethane, chloroform or ethyl acetate. Furthermore, the extracted reaction product can be purified by a usual organic chemical procedure such as recrystallization or column chromatography.

The compound of the formula (1) which can be prepared by the method of the present invention is useful as a starting material of a physiologically active compound.

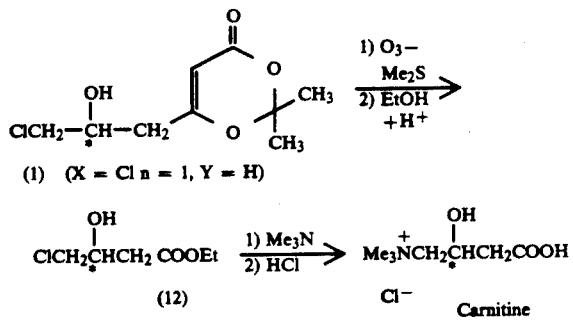

That is, the compound having the formula (1) in which X is Cl, n is 1, and Y is a hydrogen atom can be easily converted into ethyl 4-chloro-3-hydroxybutanoate (12) by ozone oxidation and then esterification, as shown by the above-mentioned chemical formulae. This compound of the formula (12) can be introduced into carnitine in accordance with a process described in C. J. Sir et al., J. Org. Chem. Soc., 105. 5925 (1983).

When the (+) form or the (−) form of the optically active compound of the starting material represented by the formula (12) is suitably selected, L-carnitine or D-carnitine can be selectively obtained. It is known that L-carnitine functions to accelerate the internal secretion from the digestive organ and to lower a blood sugar value and a cholesterol value in blood, and in short L-carnitine functions to normalize metabolism. Thus, it is fair to say that L-carnitine is a useful compound.

In addition, the compound of the formula (1) in which n is 3 can be easily converted into an eight-membered ring ether compound (13) by heating the same at 100° C. in toluene, as shown by the following reaction formula. This compound of the formula (13) is the central skeleton of natural compounds in the ocean such as lorencin, laurenyne, laurepinnacin and pinnatifidenyne to which much attention has been paid in recent years. These useful oceanic natural compounds and similar compounds can be synthesized by utilizing the procedure of the present invention.

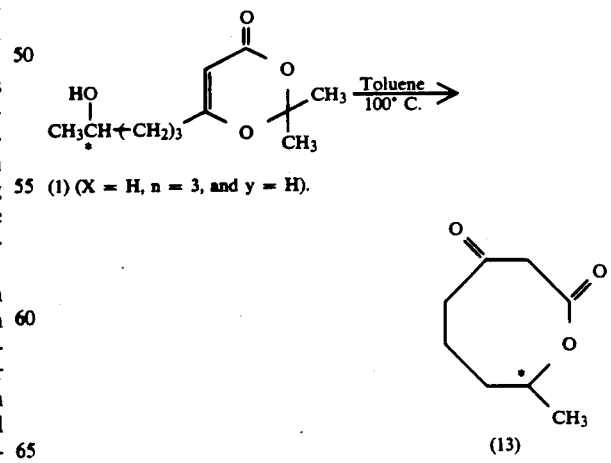

(1) (X = H, n = 3, and y = H).

[N. A. Petasis et al., J. Chem. Soc., Chem. Commun., 11, 836 (1990)].

The present invention can provide novel compounds of optically active 1,3-dioxin-4-ones represented by the formula (1), and a method for preparing the same. These compounds are useful as starting materials for physiologically active compounds and functional materials.

Now, the present invention will be described in detail in reference to examples. It is to be noted that the scope of the present invention should not be limited to these examples.

EXAMPLE 1

Asymmetrical reduction reaction of 2,2-dimethyl-6-(3-chloro-2-oxopropyl)-1,3-dioxin-4-one [a compound having the formula (6) in which n is 1, X is Cl, and a substituent is present at the 6-position] by the use of baker's yeast:

[First Step] Synthesis of 2,2-dimethyl-6-(3-chloro-2-oxopropyl)-1,3-dioxin-4-one [a compound having the formula (6) in which n is 1, X is Cl, and a substituent is present at the 6-position]:

In an argon gas stream, 20.6 ml of n-butyl lithium (1.6M solution in hexane) were added to 60 ml of an ether solution containing 3.53 g (0.033 mol) of diisopropylamine at −20° C. to form LDA. After stirring for 30 minutes, a mixture of 4.26 g (0.03 mol) of 2,2-dimethyl-6-methyl-1,3-dioxin-4-one and 60 ml of ether as well as 60 ml of an ether solution containing 1.69 g (0.015 mol) of chloroacetyl chloride were added to LDA. After the temperature was gradually returned to room temperature, 10% hydrochloric acid was added thereto to neutralize the solution, and extraction was then carried out with ether. The resultant organic layer was dried over anhydrous magnesium sulfate. Next, the solvent was distilled off, and the residue was then subjected to column chromatography (an eluent of hexane:ethyl acetate=4:1), thereby obtaining 2.26 g (yield 69%) of 2,2-dimethyl-6-(3-chloro-2-oxopropyl)-1,3-dioxin-4-one.

m.p. 64.5° to 65° C.

Elementary Analysis: Calcd.: C 49.42%; H 5.07%; Cl 16.23%. Found: C 49.46%; H 5.11%; Cl 16.40%.

IR(CHCl$_3$): 1730, 1645 cm$^{-1}$.

$^1$H-NMR (CDCl$_3$) δ: 1.73 (6H, s), 3.59 (2H, s), 4.18 (2H, s), 5.40 (1H, s).

[Second Step] Asymmetrical reduction of 2,2-dimethyl-6-(3-chloro-2-oxopropyl)-1,3-dioxin-4-one by the use of baker's yeast:

30 g of baker's yeast (made by Oriental Yeast Co., Ltd.) and 15 g of saccharose were added in 30 ml of tap water, and the solution was then stirred at 32° C. for 30 minutes. Afterward, 300 mg of 2,2-dimethyl-6-(3-chloro-2-oxopropyl)-1,3-dioxin-4-one obtained in the above-mentioned first step were added thereto, and the solution was then stirred at the same temperature overnight. 7.5 g of saccharose were further added thereto, followed by stirring overnight. Water of the reaction solution was then distilled off under reduced pressure, and the resultant residue was extracted with dichloromethane and then dried over anhydrous sodium sulfate. Afterward, the solvent was distilled off, and the residue was then subjected to column chromatography (an eluent of hexane:ethyl acetate=4:1), thereby obtaining 106 mg (yield 35%) of (−)-2,2-dimethyl-6-(3-chloro-2-hydroxypropyl)-1,3-dioxin-4-one [a compound having the formula (1) in which n is 1, X is Cl, Y is a hydrogen atom, and a substituent is present at the 6-position].

$[\alpha]_D^{24}$ −8.9° (c 0.65, CHCl$_3$).

IR(CHCl$_3$): 3160, 1725, 1640 cm$^{-1}$.

$^1$H-NMR (CDCl$_3$) δ: 1.87 (6H, s), 2.52 (2H, d), 2.87–3.29 (1H, br), 3.62 (2H, d), 4.18 (1H t t), 5.40 (1H, s).

According to measurement by HPLC using CHIRALCEL OD (Daisel Chemical Industries, Ltd.), it was confirmed that the optical purity of the product was 46% ee.

EXAMPLE 2

Asymmetrical reduction reaction of 2,2-dimethyl-6-(3-benzyloxy-2-oxopropyl)-1,3-dioxin-4-one [a compound having the formula (6) in which n is 1, X is a benzyloxy group, and a substituent is present at the 6-position] by the use of baker's yeast:

[First Step] Synthesis of 2,2-dimethyl-6-(3-benzyloxy-2-oxopropyl)-1,3-dioxin-4-one:

In an argon gas stream, 13.75 ml of n-butyl lithium (1.6M solution in hexane) were added to 60 ml of an ether solution containing 2.35 g (0.022 mol) of diisopropylamine at −20° C. to form LDA. After stirring for 30 minutes, the solution was cooled to −78° C., and 6.93 ml (0.04 mol) of HMPA were added thereto, followed by stirring for 15 minutes. Afterward, a mixture of 2.84 g (0.02 mol) of 2,2-dimethyl-6-methyl-1,3-dioxin-4-one and 60 ml of ether as well as 60 ml of an ether solution were added to LDA. After the temperature was gradually returned to room temperature, 10% hydrochloric acid was added thereto to neutralize the solution, and extraction was then carried out with ether. The resultant organic layer was dried over anhydrous magnesium sulfate. Next, the used solvent was distilled off, and the residue was then subjected to column chromatography (an eluent of hexane:ethyl acetate=4:1), thereby obtaining 1.95 g (yield 67%) of 2,2-dimethyl-6-(3-benzyloxy-2-oxopropyl)-1,3-dioxin-4-one.

IR(CHCl$_3$): 1735, 1645 cm$^{-1}$.

$^1$H-NMR (CDCl$_3$) δ: 1.76 (6H, s), 3.50 (2H, s), 4.11 (2H, s), 4.73 (2H, s), 5.33 (1H, s), 7.36 (6H s).

[Second Step] Asymmetrical reduction of 2,2-dimethyl-6-(3-benzyloxy-2-oxopropyl)-1,3-dioxin-4-one by the use of baker's yeast:

30 g of baker's yeast (made by Oriental Yeast Co., Ltd.) and 15 g of saccharose were added in 30 ml of tap water at 32° C., and the solution was then stirred for 30 minutes. Afterward, 300 mg of 2,2-dimethyl-6-(3-benzyl-2-oxopropyl)-1,3-dioxin-4-one were added thereto, and the solution was then stirred overnight at the same temperature. 7.5 g of saccharose were further added thereto, followed by stirring overnight. Water of the reaction solution was then distilled off under reduced pressure, and the residue was extracted with dichloromethane and then dried over anhydrous sodium sulfate. Afterward, the solvent was distilled off, and the residue was then subjected to column chromatography (an eluent of hexane:ethyl acetate=4:1), thereby obtaining 168 mg (yield 56%) of (−)-2,2-dimethyl-6-(3-benzyloxy-2-hydroxypropyl)-1,3-dioxin-4-one [a compound having the formula (1) in which n is 1, X is a benzyloxy group, Y is a hydrogen atom, and a substituent is present at the 6-position].

$[\alpha]_D^{24}$ −8.72° (c 1.81, CHCl$_3$).

IR(CHCl$_3$): 3450, 1730, 1640 cm$^{-1}$.

$^1$H-NMR (CDCl$_3$) δ: 66 (6H, s), 2.40 (2H, d), 3.35–3.83 (2H, m), 3.50 (1H, br), 3.95–4.24 (1H, m), 4.56 (2H, s), 5.33 (1H, s), 7.33 (5H, s).

According to measurement by HPLC using CHIRALCEL OD (made by Daisel Chemical Industries, Ltd.), it was confirmed that the optical purity of the product was 75% ee.

EXAMPLE 3

Asymmetrical reduction reaction of 2,2-dimethyl-6-(3-azido-2-oxopropyl)-1,3-dioxin-4-one [a compound having the formula (6) in which n is 1, X is $N_3$, and a substituent is present at the 6-position] by the use of baker's yeast:

[First Step] Synthesis of 2,2-dimethyl-6-(3-azido-2-oxopropyl)-1,3-dioxin-4-one:

195 mg (3.0 mmol) of sodium azide were added to 2 ml of a DMF solution containing 328 mg (1.5 mmol) of 2,2-dimethyl-6-(3-chloro-2-oxopropyl)-1,3-dioxin-4-one prepared in Example 1, followed by stirring at room temperature for 10 minutes. Afterward, the solution was poured into ice water, extracted with ether, and then dried with anhydrous magnesium sulfate. After ether was distilled off, the residue was then subjected to column chromatography (an eluent of hexane:ethyl acetate=1:1), thereby obtaining 278 mg (yield 82%) of 2,2-dimethyl-6-(3-azido-2-oxopropyl)-1,3-dioxin-4-one.

IR($CHCl_3$): 2125, 1730, 1645 $cm^{-1}$.

$^1$H-NMR ($CDCl_3$) δ: 1.72 (6H, s), 3.42 (2H, s), 4.05 (2H, s), 5.73 (1H, s).

[Second Step] Asymmetrical reduction of 2,2-dimethyl-6-(3-azido-2-oxopropyl)-1,3-dioxin-4-one by the use of baker's yeast:

30 g of baker's yeast (made by Oriental Yeast Co., Ltd.) and 15 g of saccharose were added in 30 ml of tap water, and the solution was then stirred at 32° C. for 30 minutes. Afterward, 300 mg of 2,2-dimethyl-6-(3-azido-2-oxopropyl)-1,3-dioxin-4-one were added thereto, and the solution was then stirred overnight at the same temperature. 7.5 g of saccharose were further added thereto, followed by stirring overnight. Water of the reaction solution was then distilled off under reduced pressure, and the residue was extracted with dichloromethane and then dried over anhydrous sodium sulfate. Afterward, the solvent was distilled off, and the resultant residue was then subjected to column chromatography (an eluent of hexane:ethyl acetate=4:1), thereby obtaining 67 mg (yield 22%) of (+)-2,2-dimethyl-6-(3-azido-2-hydroxypropyl)-1,3-dioxin-4-one [a compound having the formula (1) in which n is 1, X is $N_3$, Y is a hydrogen atom, and a substituent is present at the 6-position].

$[α]_D^{24}$+4.35° (c 1.93, $CHCl_3$).

IR($CHCl_3$): 2110, 1725, 1640 $cm^{-1}$.

$^1$H-NMR ($CDCl_3$) δ: 1.66 (6H, s), 2.45 (2H, d), 2.93 (1H, br), 3.23–3.63 (2H, m), 3.83–4.36 (1H, m), 5.36 (1H, s).

According to measurement by HPLC using CHIRALCEL OD (made by Daisel Chemical Industries, Ltd.), it was confirmed that the optical purity of the product was 17% ee.

EXAMPLE 4

Optical resolution of (±)-2,2-dimethyl-6-(3-chloro-2-hydroxypropyl)-1,3-dioxin-4-one [a compound having the formula (6) in which n is 1, X is Cl and, be substituent is present at the 6-position]:

A mixture of 7.0 g (31.8 mmol) of (±)-2,2-dimethyl-6-(3-chloro-2-hydroxypropyl)-1,3-dioxin-4-one, 7.0 g of Lipase PS (Amano Pharmaceutical Co., Ltd.), 2.7 g (31.8 mmol) of vinyl acetate and 500 ml of benzene was stirred at 28° C. for 7 days. Afterward, lipase was removed by filtration under suction, and the solution was then subjected to silica gel chromatography (an eluent of hexane:vinyl acetate=5:1 and later 3:1), thereby obtaining 4.12 g (yield 51%) of (+)-2,2-dimethyl-6-(3-chloro-2-hydroxypropyl)-1,3-dioxin-4-one (a compound having the formula (1) in which n was 1, X was Cl, Y was a hydrogen atom, and a substituent was present at the 6-position) having $[α]_D^{20}$+19.0° (c 1.10, $CHCl_3$) and 2.44 g (yield 36%) of (−)-2,2-dimethyl-6-(3-chloro-2-acetoxypropyl)-1,3-dioxin-4-one [a compound having the formula (1) in which n was 1, X was Cl, Y was Ac, and substituent was present at the 6-position] having $[α]_D^{20}$+0.2° (c 1.07, $CHCl_3$).

IR($CHCl_3$): 1730, 1645 $cm^{-1}$.

$^1$H-NMR ($CDCl_3$) δ: 1.71 (6H, s), 2.11 (3H, d), 2.67 (2H, d), 3.66 (2H, d), 5.07–5.53 (1H, m), 5.35 (1H, s).

According to measurement by HPLC using CHIRALCEL OD and CHIRALCEL OJ (made by Daisel Chemical Industries, Ltd.) of optical resolution columns, it was confirmed that the optical purities of these products were 96% ee and 95% ee, respectively.

Furthermore, a mixture of 900 mg (3.43 mmol) of (+)-2,2-dimethyl-6-(3-chloro-2-acetoxypropyl)-1,3-dioxin-4-one obtained above, 900 mg of Lipase MY and 150 ml of a 0.1M phosphoric acid buffer solution was stirred at 28° C. for 3 days. The solution was extracted with ethyl acetate and then dried over anhydrous magnesium sulfate. Afterward, the solvent was distilled off, and the residue was then subjected to column chromatography (an eluent of hexane:ethyl acetate=3:1), thereby obtaining 594 mg (yield 79%) of (−)-2,2-dimethyl-6-(3-chloro-2-hydroxypropyl)-1,3-dioxin-4-one (a compound having the formula (1) in which n was 1, X was Cl, Y was a hydrogen atom, and a substituent was present at the 6-position). According to measurement by HPLC using CHIRALCEL OD and CHIRALCEL OJ (made by Daisel Chemical Industries, Ltd.) of optical resolution columns, it was confirmed that the optical purity of the product was 98% ee.

EXAMPLE 5

Optical resolution of (±)-2,2-dimethyl-6-(3-chloro-2-hydroxypropyl)-1,3-dioxin-4-one [a compound having the formula (2) in which n was 1, X was Cl, and a substituent was present at the 6-position]:

A mixture of 7.0 g of (±)-2,2-dimethyl-6-(3-chloro-2-hydroxypropyl)-1,3-dioxin-4-one, 7.0 g of Lipase MY (made by The Meito Sangyo Co., Ltd.), 2.7 g (31.8 mmol) of vinyl acetate and 500 ml of benzene was stirred at 28° C. for 9 days. After removal of lipase by filtration under suction, the solution was subjected to silica gel chromatography (an eluent of hexane:ethyl acetate=5:1 and later 3:1), thereby obtaining 3.81 g (yield 55%) of (−)-2,2-dimethyl-6-(3-chloro-2-hydroxypropyl)-1,3-dioxin-4-one [a compound having the formula (1) in which n was 1, X was Cl, Y was a hydrogen atom, and a substituent was present at the 6-position] having $[α]_D^{20}$−8.4° (c 1.02, $CHCl_3$) and 1.63 g (yield 24%) of (+)-2,2-dimethyl-6-(3-chloro-2-acetoxypropyl)-1,3-dioxin-4-one [a compound having the formula (1) in which n was 1, X was Cl, Y was Ac, and substituent was present at the 6-position] having $[α]_D$+0.4° (c 1.66, $CHCl_3$).

IR($CHCl_3$): 1730, 1645 $cm^{-1}$.

$^1$H-NMR ($CDCl_3$) δ: 1.71 (6H, s), 2.11 (3H, d), 2.67 (2H, d), 3.66 (2H, d), 5.07–5.53 (1H, m), 5.35 (1H, s).

According to measurement by HPLC using CHIRALCEL OD and CHIRALCEL OJ (made by Daisel Chemical Industries, Ltd.) of optical resolution columns, it was confirmed that the optical purities of these products were 49% ee and 95% ee, respectively.

EXAMPLE 6

Optical resolution of (±)-2,2-dimethyl-6-(3-chloro-2-hydroxypropyl)-1,3-dioxin-4-one [a compound having the formula (2) in which n was 1, X was Cl, and a substituent was present at the 6-position]:

A mixture of 7.0 g of (±)-2,2-dimethyl-6-(3-chloro-2-hydroxypropyl)-1,3-dioxin-4-one, 7.0 g of Lipase PS (made by Amano Pharmaceutical Co., Ltd.), and 500 ml of vinyl acetate was stirred at 28° C. for 7 days. After removal of lipase by filtration under suction, the solution was subjected to silica gel chromatography (an eluent of hexane:vinyl acetate=5:1 and later 3:1), thereby obtaining 3.86 g (yield 47%) of (+)-2,2-dimethyl-6-(3-chloro-2-hydroxypropyl)-1,3-dioxin-4-one [a compound having the formula (1) in which n was 1. X was Cl, Y is a hydrogen atom, and a substituent was present at the 6-position] having $[\alpha]_D^{20}+19.3°$ (c 1.67, CHCl$_3$) and 3.39 g (yield 49%) of (+)-2,2-dimethyl-6-(3-chloro-2-acetoxypropyl)-1,3-dioxin-4-one [a compound having the formula (1) in which n was 1, X was Cl, Y was Ac, and a substituent was present at the 6-position]having $[\alpha]_D+0.14°$ (c 1.20, CHCl$_3$).

IR(CHCl$_3$): 1730, 1645 cm$^{-1}$.

$^1$H-NMR (CDCl$_3$) δ: 1.71 (6H, s), 2.11 (3H, d), 2.67 (2H, d), 3.66 (2H, d), 5.07–5.53 (1H, m), 5.35 (1H, s).

According to measurement by HPLC using CHIRALCEL OD and CHIRALCEL OJ (made by Daisel Chemical Industries, Ltd.) of optical resolution columns, it was confirmed that the optical purities of these products were 98% ee and 94% ee, respectively.

EXAMPLE 7

Optical resolution of (±)-2,2-dimethyl-6-(3-chloro-2-acetoxypropyl)-1,3-dioxin-4-one [a compound having the formula (5) in which n was 1, X was Cl, and a substituent was present at the 6-position]:

A mixture of 0.9 g (3.43 mmol) of (±)-2,2-dimethyl-6-(3-chloro-2-hydroxypropyl)-1,3-dioxin-4-one, 0.9 g of Lipase PS, 150 ml of a 0.1M phosphoric acid buffer solution (pH 7.2) and 450 ml of acetone was stirred at 28° C. for 3 hours. After the product was extracted with ethyl acetate, the solvent was distilled off, and the residue was subjected to silica gel chromatography (an eluent of hexane:vinyl acetate=3:1), thereby obtaining 27 mg (yield 3%) of (−)-2,2-dimethyl-6-(3-chloro-2-hydroxypropyl)-1,3-dioxin-4-one [a compound having the formula (1) in which n was 1, X was Cl, Y was a hydrogen atom, and a substituent was present at the 6-position] and 0.48 g (yield 53%) of (−)-2,2-dimethyl-6-(3-chloro-2-acetoxypropyl)-1,3-dioxin-4-one [a compound having the formula (1) in which n was 1, X was Cl, Y was Ac, and a substituent was present at the 6-position].

EXAMPLE 8

Asymmetric reduction reaction of 2,2-dimethyl-6-(4-oxopentyl)-1,3-dioxin-4-one [a compound having the formula (6) in which n was 3, X was a hydrogen atom, and a substituent was present at the 6-position] by the use of baker's yeast:

[First Step] Synthesis of 2,2-dimethyl-6-(4-oxopentyl)-1,3-dioxin-4-one:

In an argon gas stream, 20.6 ml of n-butyl lithium (1.6M solution in hexane) were added to 60 ml of an ether solution containing 3.53 g (0.033 mol) of diisopropylamine at −20° C. to form LDA. After stirring for 30 minutes, the solution was cooled to −78° C., and 10.4 ml (0.06 mol) of HMPA were added thereto, followed by stirring for 15 minutes. Afterward, a mixture of 4.26 g (0.03 mol) of 2,2-dimethyl-6-methyl-1,3-dioxin-4-one and 60 ml of ether as well as 60 ml of an ether solution containing 2.1 g (0.03 mol) of methyl vinyl ketone were added to the solution. After the temperature was gradually returned to room temperature, 10% hydrochloric acid was added thereto to neutralize the solution, and extraction was then carried out with ether. The resultant organic layer was dried over anhydrous magnesium sulfate. Next, the used solvent was distilled off, and the residue was then subjected to column chromatography (an eluent of hexane:ethyl acetate=4:1), thereby obtaining 3.16 g of 2,2-dimethyl-6-(4-oxopentyl)-1,3-dioxin-4-one.

EXAMPLE 9

Step] Asymmetrical reduction of 2,2-dimethyl-6-(oxopentyl)-1,3-dioxin-4-one by the use of baker's yeast:

30 g of baker's yeast (made by Oriental Yeast Co., Ltd.) and 15 g of saccharose were added in 30 ml of tap water, and the solution was then stirred at 32° C. for 30 minutes. Afterward, 300 mg of 2,2-dimethyl-6-(4-oxopentyl)-1,3-dioxin-4-one were added thereto, and the solution was then stirred overnight at the same temperature. 7.5 g of saccharose were further added thereto, followed by stirring overnight. Water of the reaction solution was then distilled off under reduced pressure, and the resultant residue was extracted with dichloromethane and then dried over anhydrous sodium sulfate. Afterward, the solvent was distilled off, and the resultant residue was then subjected to column chromatography (an eluent of hexane:ethyl acetate=4:1), thereby obtaining 148 mg (yield 50%) of (−)-2,2-dimethyl-6-(4-hydroxypentyl)-1,3-dioxin-4-one [a compound having the formula (1) in which n is 3, X is a hydrogen atom, Y is a hydrogen atom, and a subtituent is present at the 6-position].

According to measurement by HPLC using CHIRALCEL OD (Daisel Chemical Industries, Ltd.), it was confirmed that the optical purity of the product was 90% ee or more.

EXAMPLE 10

Asymmetric reduction of 2,2-dimethyl-5-(3-oxobutyl)-1,3-dioxin-4-one by the use of baker's yeast:

30 g of baker's yeast (made by Oriental Yeast Co., Ltd.) and 15 g of saccharose were added in 30 ml of tap water, and the solution was then stirred at 32° C. for 30 minutes. Afterward, 350 mg of 2,2-dimethyl-5-(3-oxobutyl)-1,3-dioxin-4-one were added thereto, and the solution was then stirred overnight at the same temperature. 7.5 g of saccharose were further added thereto, followed by stirring overnight. Water of the reaction solution was then distilled off under reduced pressure, and the resultant residue was extracted with dichloromethane and then dried over anhydrous sodium sulfate. Afterward, the solvent was distilled off, and the residue was then subjected to column chromatography (an eluent of hexane:ethyl acetate=4:1), thereby obtaining 161 mg (yield 55%) of (−)-2,2-dimethyl-5-(3-hydroxybutyl)-1,3-dioxin-4-one [a compound having the formula (1) in which n is 2, X is a hydrogen atom, Y is a hydrogen atom, and a substituent is present at the 5-position].

According to measurement by HPLC using CHIRALCEL OD (Daisel Chemical Industries, Ltd.), it was confirmed that the optical purity of the product was 99% ee or more.

EXAMPLE 10

(Application Example)

Preparation of optically active ethyl 4-chloro-3-hydroxybutanoate (12):

Ozone was introduced into a mixture of 225.5 mg (1 mmol) of (+)-2,2-dimethyl-(3-chloro-2-hydroxypropyl)-1,3-dioxin-4-one (96% ee) obtained in Example 4 and 20 ml of methanol at −78° C. for 5 hours, and 2 ml of dimethyl sulfide were added thereto, followed by stirring at the same temperature for 2 hours. The temperature was gradually returned to room temperature, and the solution was then stirred for 5 hours. Afterward, the solvent was distilled off, and the resultant residue was then dissolved in ethanol. 3 drops of concentrated sulfuric acid were added thereto, and the solution was then heated at 80° C. for 30 minutes. Next, ethanol was distilled off, and the residue was diluted with water. The solution was extracted with dichloromethane and then dried over anhydrous sodium sulfate, and the solvent was distilled off and the residue was then subjected to column chromatography (an eluent of hexane:ethyl acetate=5:1), thereby obtaining 109.4 mg (yield 66%) of (+)-ethyl 4-chloro-3-hydroxybutanoate.

$[\alpha]_D^{26} + 21.1°$ (c 3.11, CHCl$_3$).

Furthermore, (−)-2,2-dimethyl-(3-chloro-2-hydroxypropyl)-1,3-dioxin-4-one (98% ee) obtained in Example 4 was used as a material in accordance with a similar reaction to form (−)-ethyl -4-chloro-3-hydroxybutanoate.

$[\alpha]_D^{24} - 20.2°$ (c 1.00, CHCl$_3$).

PART II

Background of the Invention (i) Field of the Invention

The present invention relates to an optically active compound which is useful as a starting material for the synthesis of a physiologically active substance. More specifically, it relates to methods for preparing optically active 5,6-epoxyhexanoic acid ester and optically active 6-chloromethyltetrahydropyran-2-one, and a novel and optically active intermediate compound which is advantageous for the preparation of the same.

(ii) Description of the Prior Art

Optically active 5,6-epoxyhexanoic acid esters are compounds which are useful as starting materials for the various kinds of physiologically active compounds.

For example, a 5,6-epoxyhexanoic acid ester represented by the following formula (6') can be led to 5-hexanolide (a) when reacted with methyllithium as shown by the following reaction formula, and this compound (a) can be further led to 2-methyl-5-hexanolide (b) [K. Mori et al., Tetrahedron., 41. 541 (1985), and W. H. Pirkle et el., J. Org. Chem., 44, 2169 (1979)]. However, a 2R, 5S) form of the compounds having the formula (a) is the main component of the sex pheromone of *Xylocopa hirutissima*:

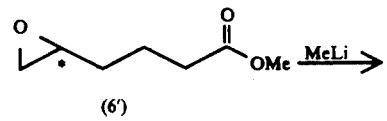

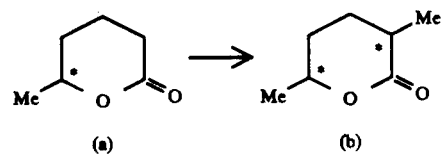

(hereinafter in this specification, the symbol * represents an asymmetric carbon atom).

Furthermore, Suzuki et al. have disclosed the synthesis of a compound (c) in which R' is a butyl group or a pentyl group and which is analogous to the compound of the formula (a) in Chem. Pharm. Bull. 38, 2381 (1980):

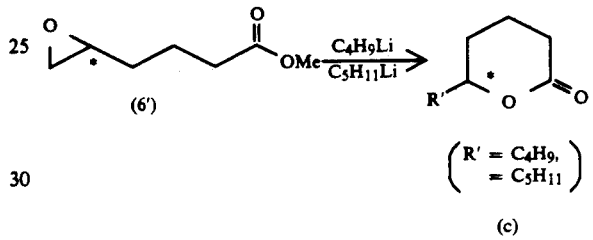

The physiologically active compound having an asymmetric carbon atom contains plural stereo isomers, but in general, only one of these isomers exerts advantageous characteristics. Therefore, when a racemic modification or a compound having a low optical purity is used as the starting material for the synthesis of the physiologically active compound, the resultant product cannot exert the sufficiently physiological activity. For this reason, it is desirable that the compound which will be fed as the starting material has the sufficiently high optical purity.

Optically active 5,6-epoxyhexanoic acid esters are known as raw materials for the synthesis of the various useful physiologically active compounds, and synthetic techniques of these esters are described in K. Mori et al., Tetrahedron, 41. 541 (1985) and M. Suzuki et al., Chem. Pharm. Bull., 38, 2381 (1990).

However, the above-mentioned ester can be synthesized from naturally occurring malic acid through reactions of 9 steps, which is not considered to be efficient. That is, for the synthesis of the ester, it is required to subject an aldehyde (e) obtained from S-(−)-malic acid (d) through 4 steps to a Horner-Wittig, reduction, the removal of acetonide, tosylate formation and epoxidation in turn:

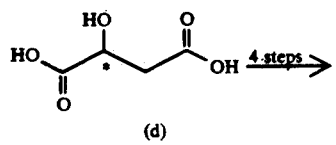

-continued

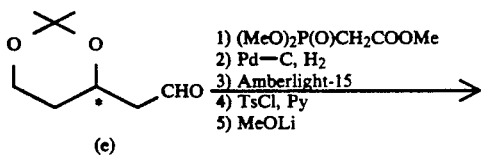

(e)

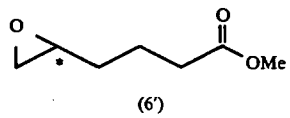

(6')

On the other hand, B. Damine et al., J. Org. Chem. 45, 3552 (1981) discloses that 6-chloromethyltetrahydropyran-2-one of the formula (g) can be synthesized by chlorinating an unsaturated acid (f) with Dichloroamine T as shown by the following reaction formula, but this technique has the problem that a racemic compound is exclusively obtained:

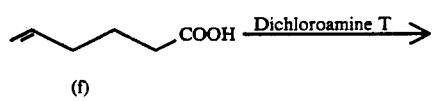

(f)

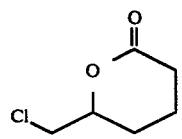

Racemic modification
(g)

SUMMARY OF THE INVENTION

An object of the present invention is to provide an optically active compound which is useful as a starting material for the synthesis of a physiologically active compound. In the concrete, the object of the present invention is to provide a method for efficiently preparing an optically active 5,6-epoxyhexanoic acid ester and its intermediate, and it is also to provide this novel and optically active intermediate compound.

The present inventors have intensively conducted research with the intention of achieving the above-mentioned objects. As a result, they have found that when optically active 2,2-dimethyl-6-(3-chloro-2-hydroxypropyl)-1,3-dioxin-4-one represented by the below-mentioned formula (1) is used as a starting material, an optically active 5,6-epoxyhexanoic acid ester having a high optical purity can be obtained, and that a novel and optically active compound which is necessary for the preparation of this ester can be obtained. In consequence, the present invention has been completed.

A method for preparing an optically active 5,6-epoxyhexanoic acid ester which is the first aspect of the present invention comprises the step of lactonizing optically active 2,2-dimethyl-6-(3-chloro-2-hydroxypropyl)-1,3-dioxin-4-one represented by the formula (1)

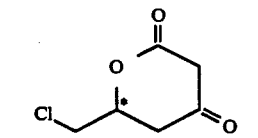

to form optically active 6-chloromethyltetrahydropyran-2,4-dione represented by the formula (2)

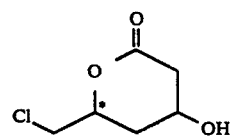

the step of reacting the thus formed compound with hydrogen in the presence of a catalyst to obtain optically active 6-chloromethyl-4-hydroxytetrahydropyran-2-one represented by the formula (3)

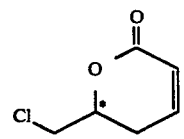

the step of subjecting this compound of the formula (3) to a dehydration reaction, thereby obtaining optically active 6-chloromethyldihydropyran-2-one represented by the formula (4)

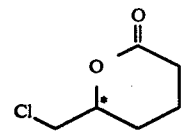

the step of reacting the compound of the formula (4) with hydrogen in the presence of a catalyst to form optically active 6-chloromethyltetrahydropyran-2-one represented by the formula (5)

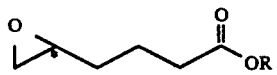

and the step of treating the compound of the formula (5) in an alcohol solvent under basic conditions to prepare an optically active 5,6-epoxyhexanoic acid ester represented by the formula (6)

(in each formula, the symbol * represents an asymmetric carbon atom, and R is a methyl group or an ethyl group).

A method for preparing optically active 6-chloromethyltetrahydropyran which is the second aspect of the present invention comprises the steps of lactonizing optically active 2,2-dimethyl-6-(3-chloro-2-hydroxypropyl)-1,3-dioxin-4-one represented by the formula (1) to form optically active 6-chloromethyltetrahydropyran-2,4-dione represented by the formula (2); reacting the compound of the formula (2) with hydrogen in the presence of a catalyst to obtain optically active 6-chloromethyl-4-hydroxytetrahydropyran-2-one represented by the formula (3); subjecting the compound of the formula (3) to a dehydration reaction to obtain optically active 6-chloromethyldihydropyran-2-one represented by the formula (4); and reacting the compound of the formula (4) with hydrogen in the presence of a catalyst to obtain optically active 6-chloromethyltetrahydropyran-2-one represented by the formula (5).

In the present invention, the third aspect is directed to optically active 6-chloromethyltetrahydropyran-2,4-dione represented by the formula (2), the fourth aspect is directed to optically active 6-chloromethyl-4-hydroxytetrahydropyran-2-one represented by the formula (3), the fifth aspect is directed to optically active 6-chloromethyldihydropyran-2-one represented by the formula (4), and the sixth aspect is directed to optically active 6-chloromethyltetrahydropyran-2-one represented by the formula (5).

DETAILED DESCRIPTION OF THE INVENTION

A method for preparing an optically active 5,6-epoxyhexanoic acid ester of the present invention will be described in more detail. In the first step, a reaction represented by the following reaction formula is carried out:

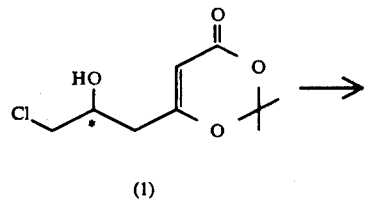

(1)

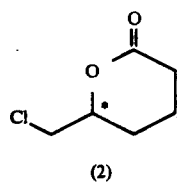

(2)

That is, 2,2-dimethyl-6-(3-chloro-2-hydroxypropyl)-1,3-dioxin-4-one represented by the formula (1) is treated under basic conditions to carry out the removal of acetonide and lactonization in the first step, whereby a compound represented by the formula (2) can be obtained. In this step, examples of the usable base include potassium carbonate, sodium carbonate, calcium carbonate, potassium hydroxide and sodium hydroxide. Furthermore, examples of the solvent include methanol, ethanol, hexane, butane, benzene, toluene and THF. A reaction temperature may be room temperature, but it is also possible to curtail a reaction time by performing the reaction at a reflux temperature.

In the second step, the reaction shown by the following reaction formula is carried out:

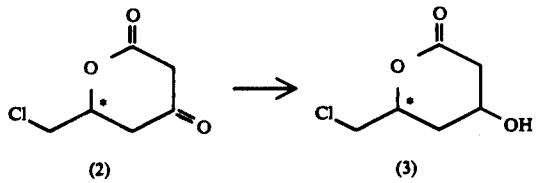

That is, the compound represented by the formula (2) is allowed to act on a general-purpose catalyst such as a palladium catalyst or a platinum catalyst under a hydrogen atmosphere, whereby the compound represented by the formula (3) can be synthesized. The reaction can sufficiently proceed at room temperature under atmospheric pressure, but it is also possible to shorten the reaction time by pressing and heating.

In the second step, the reaction shown by the following reaction formula is carried out:

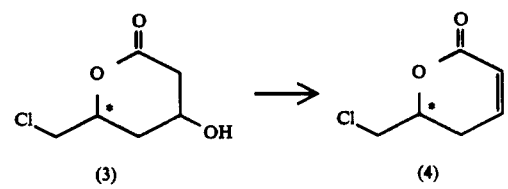

That is, optically active 6-chloromethyl-4-hydroxytetrahydropyran-2-one represented by the formula (3) is subjected to a dehydration reaction under acidic conditions to obtain 6-chloromethyldihydropyran-2-one represented by the formula (4). The removal of formed water can be achieved by an azeotropy operation using a non-aqueous solvent such as benzene or toluene or by pouring a dehydrating agent such as molecular sieves into the system.

In the fourth step, the reaction shown by the following reaction formula is carried out:

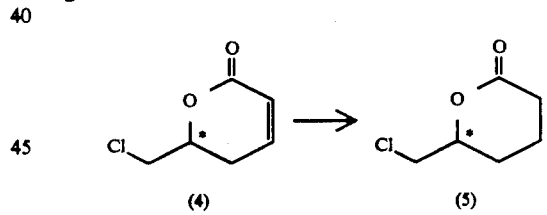

That is, 6-chloromethyldihydropyran-2-one represented by the formula (4) is allowed to act on a general-purpose catalyst such as a palladium catalyst or a platinum catalyst under a hydrogen atmosphere, whereby optically active 6-chloromethyltetrahydropyran-2-one represented by the formula (5) can be synthesized. The reaction can sufficiently proceed at room temperature under atmospheric pressure, but it is also possible to shorten the reaction time with pressing and heating.

In the fifth step, the reaction shown by the following formula is carried out:

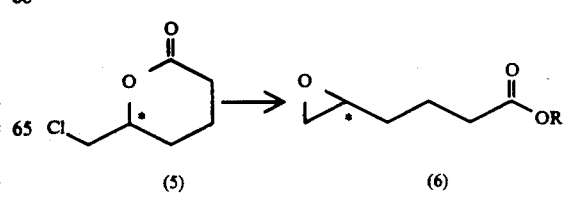

That is, 6-chloromethyltetrahydropyran-2-one represented by the formula (5) is treated under basic conditions to obtain an optically active 5,6-epoxyhexanoic acid ester represented by the formula (6) in one step. In this step, examples of the usable base include potassium carbonate, sodium carbonate, calcium carbonate, potassium hydroxide and sodium hydroxide. Furthermore, examples of the solvent include methanol and ethanol. Here, when methanol is used as the solvent, the compound of the formula (6) in which R is methyl can be obtained, and when ethanol is used, the compound of the formula (6) in which R is ethyl can be obtained. The reaction temperature may be room temperature, but it is also possible to shorten the reaction time by reacting at a reflux temperature.

Moreover, both the optical antipodes of optically active 2,2-dimethyl-6-(3-chloro-2-hydroxypropyl)-1,3-dioxin-4-one represented by the formula (1) which can be used in the preparation method regarding the first aspect of the present invention can be selectively employed to selectively form both the optical antipodes of the optically active 5,6-epoxyhexanoic acid ester represented by the formula (6).

The optically active compounds of the present invention are intermediate compounds in the first preparation method of the present invention, and these optically active compounds are optically active 6-chloromethyltetrahydropyran-2,4-dione represented by the formula (2), optically active 6-chloromethyl-4-hydroxytetrahydropyran-2-one represented by the formula (3), optically active 6-chloromethyldihydropyran-2-one represented by the formula (4), and optically active 6-chloromethyltetrahydropyran-2-one represented by the formula (5).

The preparation of these optically active compounds of the present invention can be achieved by carrying out the reactions in necessary several steps of the preparation method of the above-mentioned optically active 5,6-epoxyhexanoic acid ester of the present invention. In addition, both the optical antipodes of optically active 2,2-dimethyl-6-(3-chloro-2-hydroxypropyl)-1,3-dioxin-4-one represented by the formula (1) can be selectively employed to selectively form both the optical antipodes of each of the optically active compounds which are the intermediates.

The second preparation method of the present invention is a preparation method in which optically active 6-chloromethyltetrahydropyran-2-one of the formula (5) is produced from the starting material, i.e., the compound of the formula (1) via the compounds represented by the formulae (2), (3) and (4) in the above-mentioned first preparation method.

According to the present invention, there is provided an efficient method having less synthetic steps which can prepare an optically active 5,6-epoxyhexanoic acid ester which is useful as the starting material for the synthesis of a physiologically active compound.

Furthermore, according to the present invention, there are provided optically active 6-chloromethyltetrahydropyran-2,4-dione represented by the formula (2), optically active 6-chloromethyl-4-hydroxytetrahydropyran-2-one represented by the formula (3), optically active 6-chloromethyltetrahydropyran-2-one represented by the formula (4), and optically active 6-chloromethyltetrahydropyran-2-one represented by the formula (5) which are novel and optically active compounds and which are necessary for the above-mentioned preparation method.

EXAMPLES

Now, the present invention will be described in more detail in reference to examples. The scope of the present invention should not be limited to these examples.

EXAMPLE 1

Preparation of (−)-6-chloromethyltetrahydropyran-2,4-dione [a compound of the formula (2)]:

A mixture of 940 mg (4.26 mmol) of (−)-2,2-dimethyl-6-(3-chloro-2-hydroxypropyl)-1,3-dioxin-4-one (98% ee), 882 mg (6.39 mmol) of potassium carbonate and 10 ml of methanol was stirred at room temperature for 12 hours. After completion of the reaction, methanol was distilled off, and the resultant residue was neutralized with 10% HCl and then extracted with ethyl acetate, followed by drying over anhydrous magnesium sulfate. After the solvent was distilled off, the residue was subjected to column chromatography (an eluent of hexane:ethyl acetate=3:1), thereby obtaining 510 mg (yield 74%) of (−)-6-chloromethyltetrahydropyran-2,4-dione.

m.p. 98° to 99° C.
$[\alpha]_D^{25}$ −82.6° (C, 0.29, MeOH).
Elementary Analysis: Calcd.: C 44.44%; H 4.35%; Cl 21.58%; Found: C 44.54%; H 4.27%; Cl 21.57%.
IR(CHCl$_3$): 1775, 1740 cm$^{-1}$.
$^1$H-NMR δ: 2.62–2.95 (2H, m), 3.12–4.28 (4H, m), 4.58–5.38 (1H, m).

EXAMPLE 2

Preparation of (+)-6-chloromethyltetrahydropyran-2,4-dione [a compound of the formula (2)]:

A mixture of 470 mg (2.13 mmol) of (+)-2,2-dimethyl-6-(3-chloro-2-hydroxypropyl)-1,3-dioxin-4-one (99% ee), 441 mg (3.20 mmol) of potassium carbonate and 5 ml of methanol was stirred at room temperature for 9 hours. After completion of the reaction, methanol was distilled off, and the resultant residue was neutralized with 10% HCl, extracted with ethyl acetate, and then dried over anhydrous magnesium sulfate. After the solvent was distilled off, the residue was subjected to column chromatography (an eluent of hexane:ethyl acetate=3:1), thereby obtaining 270 mg (yield 79%) of (+)-6-chloromethyltetrahydropyran-2,4-dione.

m.p. 98° to 99° C.
$[\alpha]_D^{25}$ −83.4° (C, 1.07, MeOH).
Elementary Analysis: Calcd.: C 44.44%; H 4.35%; Cl 21.58%; Found: C 44.54%; H 4.27%; Cl 21.57%.
IR(CHCl$_3$): 1775, 1740 cm$^{-1}$. $^1$H-NMR δ: 2.62–2.95 (2H, m), 3.12–4.28 (4H, m), 4.58–5.38 (1H, m).

EXAMPLE 3

Preparation of (+)-6-chloromethyl-4-hydroxytetrahydropyran-2-one [compound of the formula (3)]:

A mixture of 270 mg (1.66 mmol) of (−)-6-chloromethyltetrahydropyran-2,4-dione obtained in Example 1, 10 mg platinum dioxide and 100 ml of ethyl acetate was stirred for 7 hours under hydrogen atmosphere. After completion of the reaction, the catalyst was removed by filtration, and the solvent was distilled off to obtain 199.6 mg (yield 73%) of (+)-6-chloromethyl-4-hydroxytetrahydropyran-2-one [a compound of the formula (3)] having
$[\alpha]_D^{20}$ +13.3° (C, 1.25, CHCl$_3$).
IR(CHCl$_3$): 1735, 3425 cm$^{-1}$.

$^1$H-NMR δ: 1.65 (1H, br), 1.79–1.87 (1H, m), 2.37–2.43 (1H, m), 2.52 (1H, dd), 2.93 (1H, dd), 3.68–3.76 (2H, m), 4.28–4.35 (1H, m), 4.45–4.51 (1H, m).

and 48.1 mg (yield 20%) of (−)-6-chloromethyltetrahydropyran-2-one [a compound of the formula (5)] having
$[α]_D^{20}$ −0.77° (C, 1.03, CHCl$_3$).
IR(CHCl$_3$): 1740 cm$^{-1}$.
$^1$H-NMR δ: 1.58–2.12 (4H, m), 2.41–2.53 (1H, m), 2.60–2.67 (1H, m), 3.63 (1H, dd), 3.69 (1H, dd), 4.50–4.56 (1H, m).

EXAMPLE 4

Preparation of (−)-6-chloromethyldihydropyran-2-one [a compound of the formula (4)]:

A mixture of 50 mg (0.304 mmol) of (+)-6-chloromethyl-4-hydroxytetrahydropyran-2-one obtained in Example 3, 57.8 mg (0.304 mmol) of p-toluenesulfonic acid and 5 ml of benzene was refluxed for 30 minutes. After completion of the reaction, benzene was distilled off and distilled water were added thereto, and the solution was extracted with dichloromethane, followed by drying over anhydrous magnesium sulfate. After the solvent was distilled off, the resultant residue was subjected to column chromatography (an eluent of hexane:ethyl acetate=4:1), thereby obtaining 35.8 mg (yield 81%) of (−)-6- chloromethyldihydropyran-2-one.
$[α]_D^{23}$ −144.8° (C, 3.09, CHCl$_3$).
IR(CHCl$_3$): 1730 cm$^{-1}$.
$^1$H-NMR δ: 2.54–2.59 (2H, m), 2.71 (1H, dd), 3.76 (1H, dd), 4.64–4.71 (1H, m), 6.05–6.09 (1H, m), 6.91–6.95 (1H, m).

EXAMPLE 5

Preparation of (−)-6-chloromethyltetrahydropyran-2-one [a compound of the formula (5)]:

A mixture of 150 mg (1.024 mmol) of (−)-6-chloromethyldihydropyran-2-one obtained in Example 4, 6 ml of ethyl acetate and 60 mg of 10% palladium-carbon was stirred for 2 hours under hydrogen atmosphere. After completion of the reaction, the catalyst was removed by filtration, and the solvent was distilled off. Afterward, the resultant residue was subjected to column chromatography (an eluent of hexane:ethyl acetate=5:1), thereby obtaining 146 mg (yield 96%) of (−)-6-chloromethyltetrahydropyran-2-one having
$[α]_D^{20}$ −0.77° (C, 1.00, CHCl$_3$).
IR(CHCl$_3$) 1740 cm$^{-1}$.
$^1$H-NMR δ: 1.58–2.12 (4H, m), 2.41–2.53 ((1H, m), 2.60–2.67 (1H, m), 3.63 (1H, dd), 3.69 (1H, dd), 4.50–4.56 (1H, m).

EXAMPLE 6

Preparation of (−)-methyl 5,6-epoxyhexanoate [a compound of the formula (6) in which R is a methyl group (formula 6′)]:

67.9 mg (0.492 mmol) of potassium carbonate were added to a mixture of 48.7 mg (0.328 mmol) of (−)-6-chloromethyltetrahydropyran-2-one obtained in Example 5 and 1 ml of methanol under water cooling, and the solution was then stirred for 30 minutes and further at room temperature for 5 hours. After distilling off with methanol, 10% hydrochloric acid was added to the resultant residue to neutralize the same, and it was then extracted with dichloromethane, followed by drying over anhydrous magnesium sulfate. The solvent was distilled off to obtain 35.4 mg (yield 75%) of pure (−)-methyl 5,6-epoxyhexanoate [a compound of the formula (6′)] as the residue. The values of physical properties of this product were good and comparable to those of literature [M. Suzuki et al., Chem. Pharm. Bull., 38, 2381 (1990)].
$[α]_D^{24}$ −13.6° (C, 1.94, CHCl$_3$) {Literature value $[α]_D^{24}$ −16.2 ° (C, 0.58, CHCl$_3$)}.
IR(CHCl$_3$) 1740 cm$^{-1}$ (literature value 1740).
$^1$H-NMR δ: 1.49–1.87 (4H, m), 2.39 (2H, t), 2.48 (1H, dd), 2.75 (1H, dd), 2.92 (1H, m), 3.68 (3H, s) {literature value: 1.49–1.87 (4H, m), 2.39 (2H, t), 2.48 (1H, dd), 2.75 (1H, dd), 2.92 (1H, m), 3.68 (3H, s)}.

What is claimed is:

1. A method for preparing an optically active compound for the synthesis of a physiologically active substance which comprises lactonizing optically active 2,2-dimethyl-6-(3-chloro-2-hydroxypropyl)-1,3-dioxin-4-one represented by formula (1)

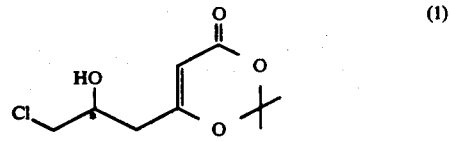

(1)

to form optically active 6-chloromethyltetrahydropyran-2,4-dione represented by formula (2)

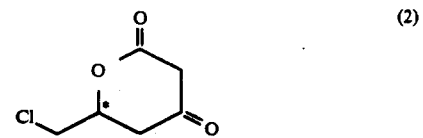

(2)

reacting the thus formed compound with hydrogen in the presence of a catalyst to obtain optically active 6-chloromethyl-4-hydroxytetrahydropyran-2-one represented by formula (3),

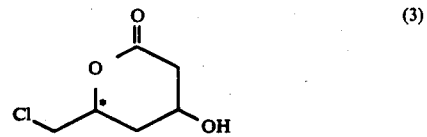

(3)

subjecting the compound of formula (3) to a dehydration reaction, thereby obtaining optically active 6-chloromethyldihydropyran-2-one represented by formula (4),

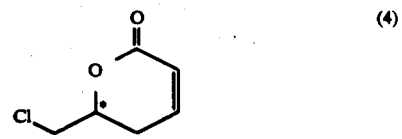

(4)

reacting the compound of formula (4) with hydrogen in the presence of a catalyst to form optically active 6-chloromethyltetrahydropyran-2-one represented by the formula (5),

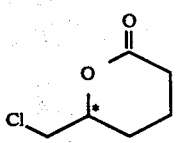

and treating the compound of the formula (5) in an alcohol solvent under basic conditions to prepare an optically active 5,6-epoxyhexanoic acid ester represented by formula (6)

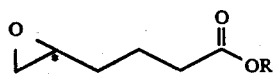

(in each formula, the symbol * represents an asymmetric carbon atom, and R is a methyl group or an ethyl group).

2. A method for preparing an optically active compound for the synthesis of a physiologically active substance which comprises lactonizing optically active 2,2-dimethyl-6-(3-chloro-2-hydroxypropyl)-1,3-dioxin-4-one represented by the formula (1)

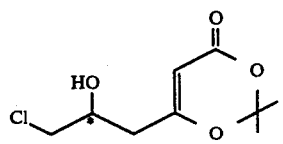

to form optically active 6-chloromethyltetrahydropyran-2,4-dione represented by the formula (2),

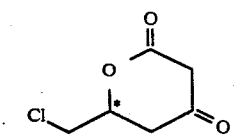

reacting the compound of formula (2) with hydrogen in the presence of a catalyst to obtain optically active 6-chloromethyl-4-hydroxytetrahydropyran-2-one represented by formula (3) ),

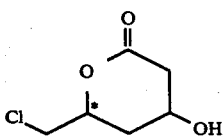

subjecting the compound of formula (3) to a dehydration reaction to obtain optically active 6-chloromethyldihydropyran-2-one represented by the formula (4),

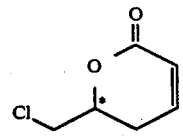

and reacting the compound of formula (4) with hydrogen in the presence of a catalyst to obtain optically active 6-chloromethyltetrahydropyran-2-one represented by formula (5)

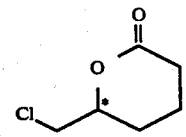

(in each formula, the symbol * represents an asymmetric carbon atom).

3. Optically active 6-chloromethyltetrahydropyran-2,4-dione represented by formula (2):

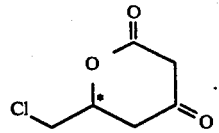

4. Optically active 6-chloromethyl-4-hydroxytetrahydropyran-2-one represented by formula (3):

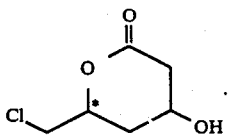

5. Optically active 6-chloromethyldihydropyran-2-one represented by formula (4):

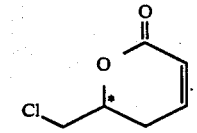

6. Optically active 6-chloromethyltetrahydropyran-2-one represented by formula (5):

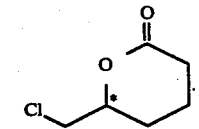

* * * * *